United States Patent
Hayashi et al.

(10) Patent No.: US 8,237,797 B2
(45) Date of Patent: Aug. 7, 2012

(54) THREE-DIMENSIONAL IMAGE OBTAINING DEVICE AND PROCESSING APPARATUS USING THE SAME

(75) Inventors: Tohoru Hayashi, Tsukuba (JP); Shozo Ishizaka, Tokyo (JP)

(73) Assignee: Rinsoken Co., Ltd., Tsukuba-shi (JP)

( * ) Notice: Subject to any disclaimer, the term of this patent is extended or adjusted under 35 U.S.C. 154(b) by 763 days.

(21) Appl. No.: 12/386,394

(22) Filed: Apr. 17, 2009

(65) Prior Publication Data

US 2009/0262183 A1 Oct. 22, 2009

(30) Foreign Application Priority Data

Apr. 21, 2008 (JP) .................................. 2008-110769

(51) Int. Cl.
*G01B 11/24* (2006.01)
*G01B 11/00* (2006.01)

(52) U.S. Cl. .......... 348/154; 348/130; 348/42; 382/106; 382/285

(58) Field of Classification Search .................... 348/42, 348/47, 154, 130; 382/106, 285
See application file for complete search history.

(56) References Cited

U.S. PATENT DOCUMENTS

| | | | | |
|---|---|---|---|---|
| 5,587,583 A | * | 12/1996 | Chin et al. | 250/332 |
| 5,991,437 A | * | 11/1999 | Migdal et al. | 382/154 |
| 7,136,157 B2 | * | 11/2006 | Gomm et al. | 356/237.1 |
| 7,667,751 B2 | * | 2/2010 | Fraenkel et al. | 348/294 |
| 2007/0019075 A1 | * | 1/2007 | Gomm et al. | 348/187 |
| 2011/0144505 A1 | * | 6/2011 | Yamamoto et al. | 600/476 |
| 2011/0184277 A1 | * | 7/2011 | Ripoll Lorenzo et al. | 600/425 |

FOREIGN PATENT DOCUMENTS

| | | |
|---|---|---|
| JP | 7-199073 | 8/1995 |
| JP | 9-179037 | 7/1997 |
| JP | 9-297269 | 11/1997 |
| JP | 9-304178 | 11/1997 |

OTHER PUBLICATIONS

Holmes, T. J. et al., "Blind deconvolution of 3D transmitted light brightfield micrographs", Journal of Microscopy, vol. 200, Part 2, Nov. 2000, pp. 114-127.

* cited by examiner

*Primary Examiner* — Khanh Dinh
(74) *Attorney, Agent, or Firm* — Jordan and Hamburg LLP

(57) ABSTRACT

An optical flux is radiated, which is focused at a measurement point in a specimen space, and a transmitted light amount is measured. A minute light absorption amount is measured from a transmitted light signal and a reference signal. While three-dimensionally scanning, a three-dimensional map in which light absorption amounts are represented by voxels (volume cells) is obtained. On this three-dimensional map, deconvolution processing with a light intensity distribution image in the vicinity of the measurement point being a convolution kernel is performed, so as to obtain a three-dimensional image of a specimen that is almost transparent in a non-dyed state.

11 Claims, 8 Drawing Sheets

FIG.1
(A) THREE-DIMENSIONAL MAP
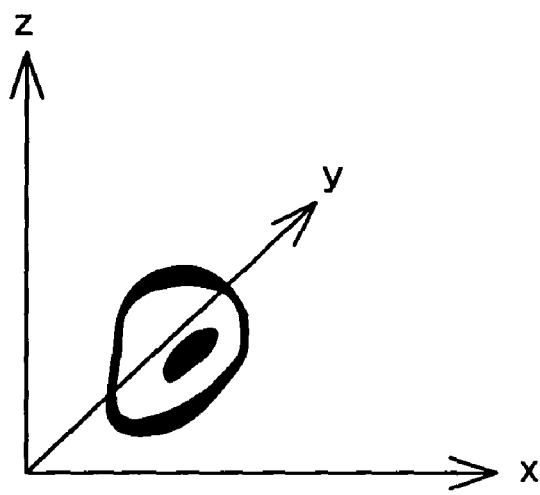
(B) THREE-DIMENSIONAL IMAGE AFTER DECONVOLUTION
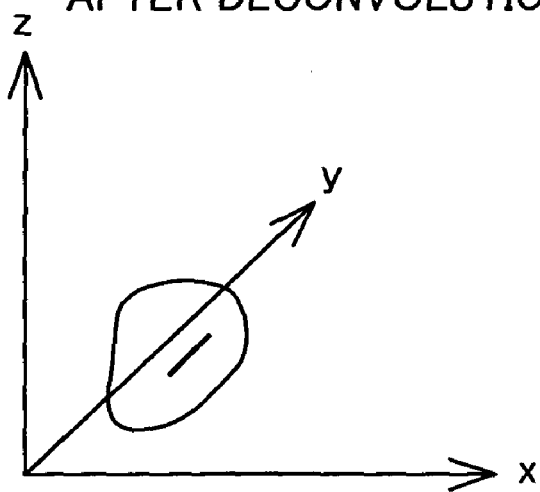

FIG.3
CONVOLUTION KERNEL
(1)
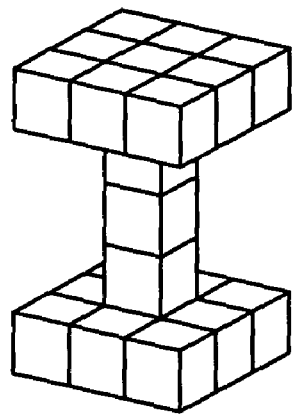
(2)
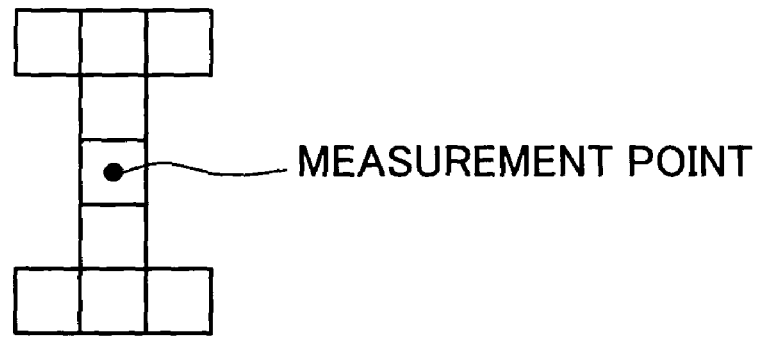

THREE-DIMENSIONAL IMAGE OBTAINING DEVICE AND PROCESSING APPARATUS USING THE SAME

BACKGROUND OF THE INVENTION

1. Field of the Invention

The present invention provides a three-dimensional image obtaining device and a method thereof for visualizing, as a specimen of a biological material having low light absorption and being almost transparent (hereinafter referred to as a biological specimen), a biological specimen of a cell and a microorganism, a sliced organ/tissue specimen.

The invention particularly relates to a three-dimensional image obtaining device applicable as an observation module forming a part of a microscope apparatus and a processing apparatus or a biomedical related measurement apparatus, and to a method thereof.

2. Description of the Related Art

There are demands for obtaining a three-dimensional image of a biological specimen such as a cell without dyeing using a florescent dye or the like. Specifically, there are demands that the observer can actually see not only the outer shape of a cell but also organelles such as nucleus in a cell.

Since the aforementioned biological specimen has low light absorption and scattering ratio and is almost transparent, it shows almost no contrast in a microscope for observing with a transmitted light. Accordingly, a phase contrast microscope or a differential interference contrast microscope which gives contrast to a biological specimen is used for observing such a specimen. An image of the biological specimen observed with these microscopes is a two-dimensional projected image and not a three-dimensional image.

Document 1 (Holmes T J, O'Connor N J, Blind deconvolution of 3D transmitted light brightfield micrographs, Journal of Microscopy, 2000, vol. 200, pt. 2, p. 114-127) discloses a microscope apparatus for detecting transmitted light intensity using an optical system of a confocal microscope. This apparatus makes a three-dimensional transmitted light map of a biological specimen, and makes a three-dimensional image of the specimen by a blind deconvolution. However, the biological specimen is almost transparent and absorbs a minute amount of light. Therefore, the three-dimensional transmitted light map only has a slight change from a three-dimensional transmitted light map when there is no specimen, and it is difficult to measure with high S/N. There are demanded an optical system that is most suitable for measuring a specimen that is almost transparent and a novel device for detecting a minute light attenuation amount.

Computed tomography (CT) using a cone beam has been reported as another method to obtain a three-dimensional image from a transmitted light. However, the CT method requires providing a rotating mechanism for shooting plural times while changing the shooting angle.

In recent years, a confocal laser scanning microscopes has been developed. JP H7-199073A discloses a confocal laser scanning microscope and an optical tomographic image displaying method thereof. The confocal laser scanning microscope can obtain a three-dimensional image when used in combination with a fluorescent dye. However, it cannot obtain a three-dimensional image in a non-dyed state.

Further, JP H9-179037A discloses a method of imaging a specific substance with a transmission laser microscope. This method is capable of obtaining a three-dimensional image. However, even with this microscope, it is not possible to image a biological specimen that is almost transparent without dyeing.

Further, JP H9-304178A discloses a transmittancy measurement technique aiming at highly accurate measurement that is not affected by inputted light intensity. The transmittancy measurement technique weights electrical signals of two light receivers and subtracts them, so as to obtain a transmittancy measurement output that becomes zero. This technique potentially has a possibility of measuring an average transmittancy of an entire specimen that is almost transparent. The disclosed technique passes a parallel optical beam through a substance to which a light is transmitted, so as to obtain an average value of the entire transmitted region. Even if a scanning function is added, the obtained image is a projected image, and a three-dimensional image is not obtained.

Furthermore, JP H9-297269A discloses a two-dimensional scanning type image input apparatus and a scanning probe microscope with black level correction. However, a specimen that is almost transparent cannot be observed by transmission.

A main object of the present invention is to provide a three-dimensional image obtaining device and a method thereof, in which a biological material that is almost transparent such as a cell is mounted in a non-dyed state as a specimen, and which are most suitable for an observation apparatus such as a microscope for visualizing a low-contrast specimen.

Another object of the present invention is to provide an apparatus for performing observation of variation over time, optical stimulation, and optical processing of a three-dimensional arbitrary point in a specimen observation region of a biological specimen that is almost transparent, which is visualized using the above three-dimensional image obtaining device.

SUMMARY OF THE INVENTION

To achieve the above-described objects, a three-dimensional image obtaining device according to the present invention, as a structure in which a biological material that is almost transparent is mounted as a specimen, for obtaining a three-dimensional image from an attenuation amount of a transmitted light through the specimen, includes a light source emitting an optical flux, a means for focusing the optical flux at a measurement point in the specimen to generate a local light intensity three-dimensional distribution in the vicinity of the measurement point, a means for three-dimensionally scanning the specimen and the measurement point relatively, a means for measuring a light attenuation amount of the optical flux from a light transmission amount of the specimen, a means for making a three-dimensional map of the light attenuation amount corresponding to position coordinates of the measurement point to be scanned, and a means for making a three-dimensional image of the specimen from the three-dimensional map by either a deconvolution using a convolution kernel obtained from a local light intensity three-dimensional distribution image in the vicinity of the measurement point or a blind deconvolution which does not initially set a convolution kernel.

With the three-dimensional image obtaining device according to the present invention, a light absorption amount of only the measurement point, which is an independent point, is obtained by deconvolution processing, and any contribution to light absorption of a peripheral portion other than the measurement point is excluded, thereby obtaining a three-dimensional image by the light absorption amount of only the measurement point. The device is structured such that the optical flux is focused at one measurement point, a local light intensity three-dimensional distribution is generated in the vicinity of the measurement point, and a convolution of a three-dimensional specimen image and the generated local light intensity three-dimensional distribution becomes a three-dimensional map obtained from an attenuation amount of a transmitted light. When voxels (volume cells) are set finely, a spatial resolution beyond diffraction limit can be obtained.

A three-dimensional processing apparatus according to the present invention includes the above-described three-dimensional image obtaining device, specifies position coordinates of an arbitrary point in a specimen space of a biological specimen that is almost transparent, and optically stimulating and/or optically processing the arbitrary point.

With the three-dimensional processing apparatus according to the present invention, it is possible to selectively stimulate and process a specific organelle, which has a minute difference in light absorption and has been conventionally difficult to be discriminated.

BRIEF DESCRIPTION OF THE DRAWINGS

FIG. 1A is an explanatory diagram of a three-dimensional map of a modulated signal voltage corresponded to three-dimensional position coordinates of a measurement point, and FIG. 1B is an explanatory diagram of a three-dimensional image after deconvolution processing from the three-dimensional map;

FIG. 3 is a diagram showing an example of a convolution kernel;

DETAILED DESCRIPTION OF THE INVENTION

The concepts of the present invention will be described.

In a biological specimen not using a dye such as a fluorescent dye, an optical flux is focused at a point in a specimen space, which is taken as a measurement point to generate a local light intensity three-dimensional distribution image in the vicinity of the measurement point. The measurement point is scanned in the specimen space, and transmitted light signals at respective points of the specimen are obtained from light transmission amounts. A three-dimensional map of light attenuation amounts is created based on a difference between a transmitted light signal and a reference signal at each point, and a three-dimensional image of the biological specimen is obtained by deconvolution processing from the three-dimensional map.

Attenuation of a transmitted light occurs due to absorption and/or scatter in a specimen. When observing a biological specimen that is almost transparent, the aforementioned attenuation of a transmitted light is small. A difference in this small light attenuation amount is observed by giving clear contrast. For brevity of description, "light absorption" to be used in the following description is expressed by including a contribution of light scatter in light absorption.

FIGS. 1A, 1B are explanatory diagrams of a three-dimensional image that is obtained finally in the present invention and a three-dimensional map of a light attenuation amount, which is intermediary measurement data before performing a deconvolution.

An optical flux for observation radiated from a light source is focused at a measurement point (X, Y, Z) set in a biological specimen space so as to generate a local light intensity three-dimensional distribution in the vicinity of the measurement point. The light attenuation amount of a light absorbed in the biological specimen is measured from the optical flux for observation which has transmitted this measurement point. While three-dimensionally scanning the entire biological specimen, measurement values of light attenuation amounts at respective measurement points are obtained. A three-dimensional map (see FIG. 1A) is obtained in which these measurement values are corresponded to three-dimensional position coordinates of the measurement points (X, Y, Z). Deconvolution processing using a convolution kernel obtained from a local light intensity three-dimensional distribution image in the vicinity of the measurement points is performed on the three-dimensional map, thereby obtaining a three-dimensional image of the biological specimen.

The three-dimensional map will be described in more detail below.

Figure 2:
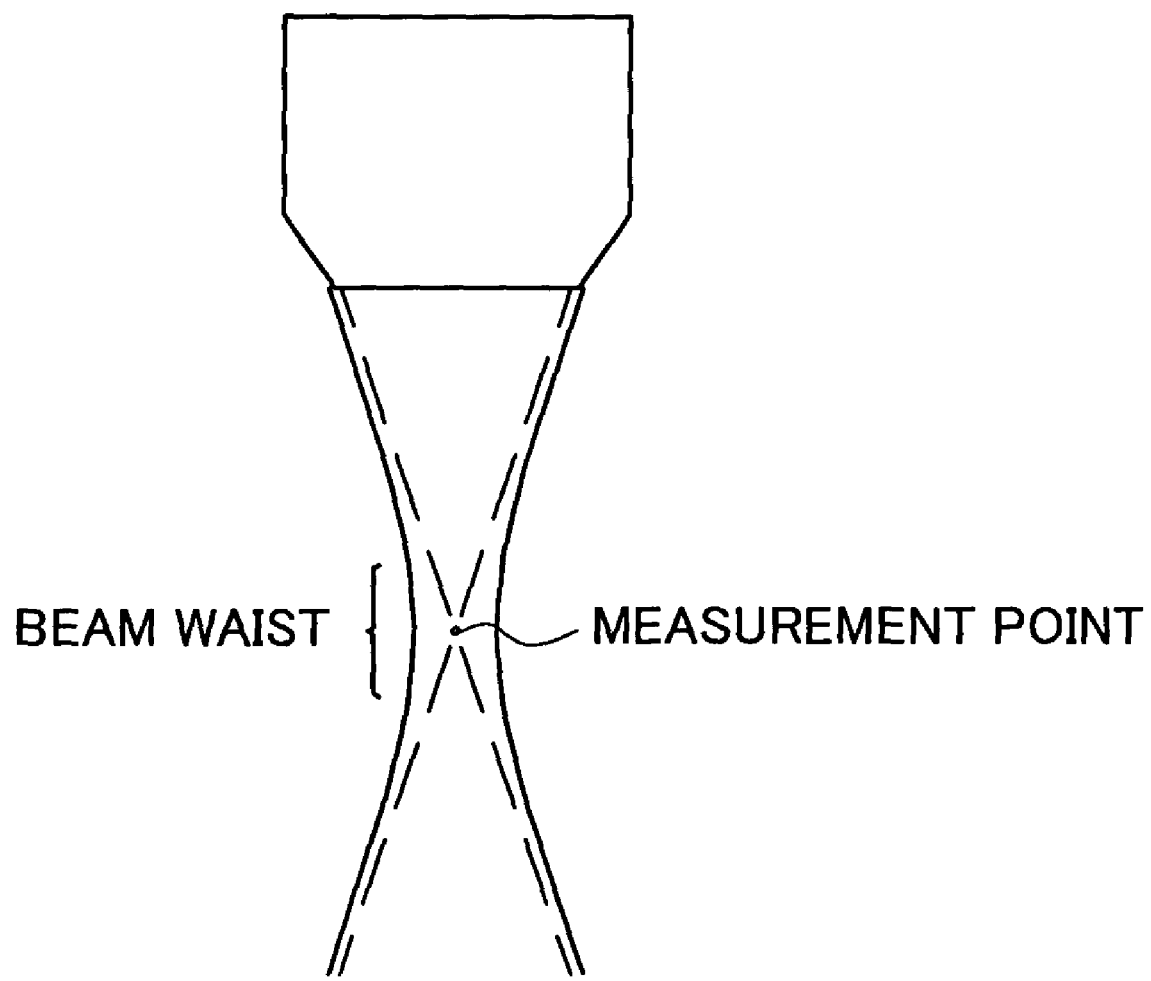
FIG. 2 is a diagram showing an optical flux in the vicinity of an enlarged measurement point.

FIG. 2 shows an optical flux in the vicinity of an enlarged measurement point. The optical flux passed through an objective lens concentrates gradually from the incident side and increases in light intensity, reaches the maximum value at a beam waist, and thereafter diffuses and decreases in light intensity. The optical flux does not concentrate at one point of a measurement point but forms a beam waist having a certain thickness. Since the beam waist exists, spreading occurs on an X-Y plane, and resolution on the X-Y plane is low. The thickness of this beam waist is determined by a numerical aperture (NA) of the objective lens. Further, a region with high light intensity exists also vertically (Z direction) of the measurement point. A light absorption amount after the optical flux transmits through the specimen is measured by adding absorption amounts at the measurement point and in a region in the vicinity of the measurement point where light intensity is high. Thus, in the Z direction, absorption in a deep range is added both upwardly and downwardly, other than the measurement point. When a three-dimensional map with the light absorption amount being voxels (volume cells) by three-dimensional scanning is displayed, only a blurred image is obtained because it is not the light absorption amount of only the measurement point and thus the resolution is too low (see FIG. 1A). When a cell is observed as a specimen for example, organelles or the like therein cannot be observed.

Here, a relationship between a true image, that is, a three-dimensional image of a target specimen and a three-dimensional map will be described in detail. The "true image" is an image shown in FIG. 1B.

The created three-dimensional map is given by a convolution (convolution integration) of the true image and a three-dimensional distribution image of local light intensity in the vicinity of the measurement point, which is an instrumental function. This approximation is satisfied only for a specimen that is almost transparent.

The approximation by a convolution will be described in detail below.

In general, a light transmitted through a specimen follows the Lambert-Beer's law, and the light attenuates by absorption. However, it can be considered that the intensity distribution of the light is constant irrespective of location, when the specimen is almost transparent and there is almost no absorption. Accordingly, a three-dimensional map (measured image) obtained by corresponding a light absorption amount, which is a difference between a signal voltage transmitted through a measurement point and a reference signal voltage, to the measurement point, can be approximated to be a convolution using, as a convolution kernel, the three-dimensional distribution (true image) of a light absorbing substance in the specimen and a local light intensity three-dimensional distribution in the vicinity of the measurement point.

The convolution kernel is set from the beam waist in the vicinity of the measurement point and portions above and below it. FIG. 3 shows an example of the convolution kernel. It is a convolution kernel constituted of 45 three dimensional voxels in total, that is, 3×3×5 in X, Y, Z directions. Each three dimensional voxel is weighted in proportion to the light intensity at its position. In FIG. 3, to make it clearly seeable, three-dimensional voxels with zero weights are omitted.

The convolution kernel is an instrumental function and is a three-dimensional distribution image of light intensity in the vicinity of the measurement point. As can be understood from the enlarged view in the vicinity of the measurement point in FIG. 2, the beam waist portion has high light intensity, and the light intensity decreases with distance from the measurement point in upper and lower portions thereof. It attenuates by approximately the square of the distance from the measurement point, and thus it should have a small error when only the measurement point and its vicinity are used for a convolution kernel and light intensity of other than a peripheral portion is zero.

The three-dimensional map (FIG. 1A) can be considered as a convolution of a three-dimensional image of a specimen (FIG. 1B), displaying of which is finally aimed at, and a convolution kernel. Therefore, the three-dimensional image of the specimen can be obtained by deconvolution, which is inverse operation of convolution. That is, the three-dimensional image of the specimen is obtained by deconvolutioning the three-dimensional map by the convolution kernel.

The approximation that is an assumption of the deconvolution processing is established when the specimen is almost transparent and has a small light absorption amount. When the light absorption amount is large, the convolution kernel varies depending on a position and has a large error. When visualizing a specimen that is almost transparent, highly accurate measurement of absorption is not necessary. That is, when visualizing a specimen that is almost transparent, the above-described error would not be a problem. FIG. 1B shows a three-dimensional image (true image) after processing to deconvolute the three-dimensional map obtained by scanning the measurement point.

Here, for comparison, it is assumed that a thin optical flux which is not focused is scanned two-dimensionally, and a three-dimensional image is obtained from a transmitted light therethrough, which is a situation similar to conventional transmission image observation. The thin optical flux penetrates the specimen and the light is absorbed according to the absorption of each three-dimensional voxel in the specimen space. An absorption amount obtained from the transmitted light is an added value of absorption amounts by respective three-dimensional voxels. The thickness of the specimen also varies depending on the position, and it is not possible to obtain the absorption of each point from the absorption amount obtained from the transmitted light.

The local light intensity three-dimensional distribution is formed locally and independently in the specimen space, and needs to be constant irrespective of position in the specimen space. This three-dimensional distribution is under a condition that the inside of the specimen space can be scanned.

When an optical flux is focused to one point of the measurement point to create the local light intensity three-dimensional distribution, the method thereof does not create a local intensity distribution that is completely independent. The light intensity attenuates before and after the optical flux reaches the measurement point, but tailing occurs. However, a portion with high light intensity is extracted and the convolution kernel is set large, so that an error thereof becomes small. To make the influence of this tailing small, it is desirable to use an optical system with a large NA, in which an optical flux concentrates rapidly and diffuses rapidly.

Hereinafter, embodiments of the present invention will be described in detail with reference to the drawings.

Figure 4:
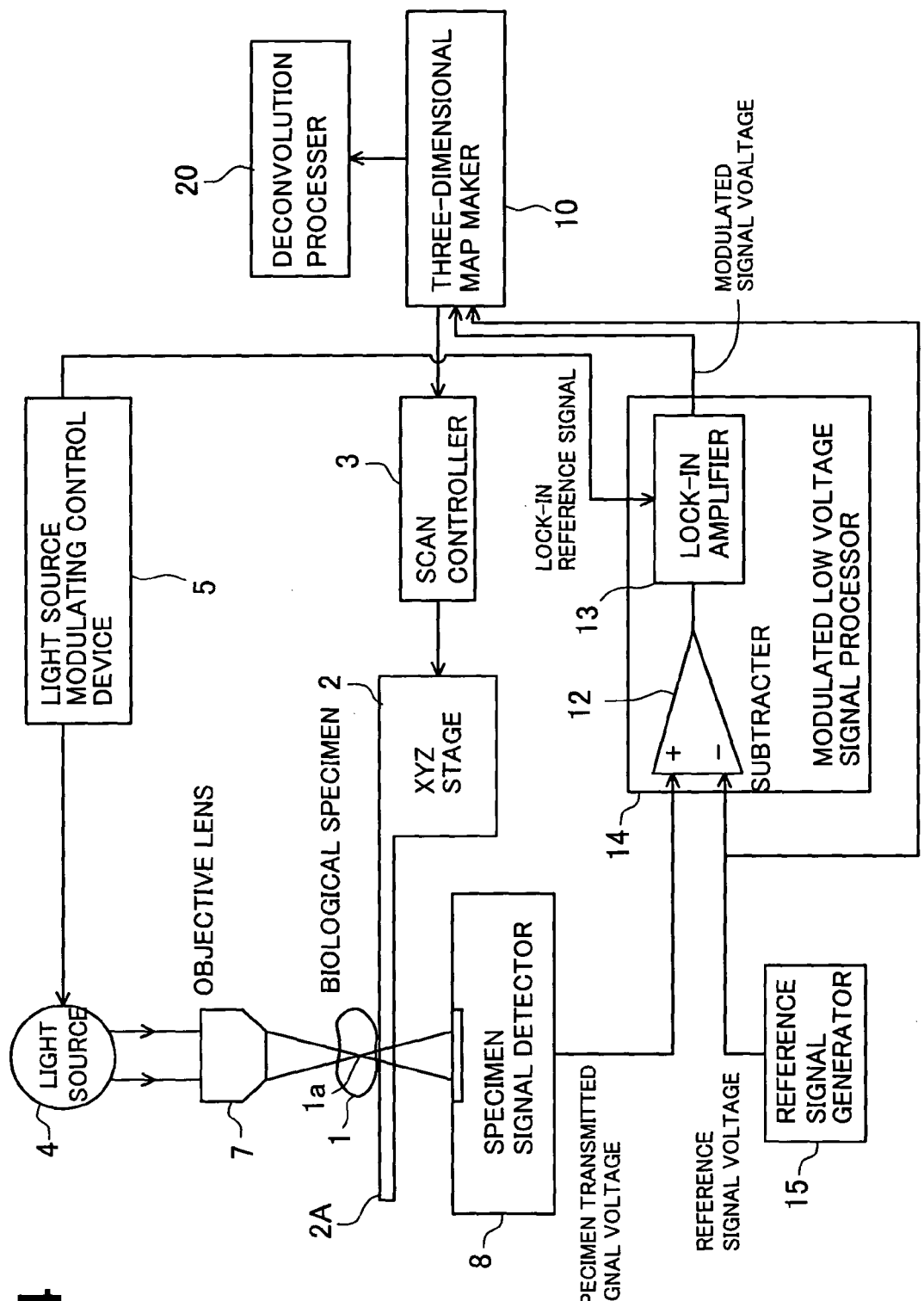
FIG. 4 is a block diagram showing a structure of a first embodiment of the present invention.

FIG. 4 shows a structure of a first embodiment and is a schematic diagram of an observation module forming a part of a biomedical related measurement apparatus. When used as an observation module, measurement in a latter stage is performed using a digital three-dimensional image obtained by the present invention.

A biological specimen 1 is mounted on a stage part 2A of an XYZ stage 2 that is three-dimensionally drivable. The stage part 2A is made of a transparent material with high light transmittance. The XYZ stage 2 is controlled by a scan controller 3 which operates by instruction from a three-dimensional map maker 10. A light source 4 is formed of an LED with a wavelength of 405 nanometers for example. The light source 4 is amplitude modulated by a predetermined frequency, for example 20 kHz, by a light source modulating control device 5, and radiates an optical flux for observation.

The optical flux for observation is focused at a measurement point 1a set in the biological specimen 1 via an objective lens 7, transmits through the biological specimen, and is incident on a specimen transmitted signal detector 8. The specimen transmitted signal detector 8 photoelectrically converts the optical flux for observation and outputs a specimen transmitted signal voltage. A reference signal generator 15 is a voltage source set in advance to a predetermined voltage. This voltage source is set so as to output a reference signal voltage equivalent to a specimen transmitted signal of when the specimen absorbs no light at all.

A modulated low voltage signal processor 14 amplifies, from a differential signal voltage between the specimen transmitted signal voltage and the reference signal voltage obtained by a subtracter 12, only a signal in synchronization with a modulation frequency (20 kHz) of the light source 4 by a lock-in amplifier 13, so as to obtain a modulated signal voltage equivalent to a light attenuation amount generated by absorption in the specimen. A light source modulation signal having a predetermined frequency for modulating the light source 4 is input to the lock-in amplifier 13 as a lock-in reference signal. The lock-in amplifier includes a phase adjusting function. The phase adjusting function matches phases of the lock-in reference signal and the differential signal that is an output of the subtracter 12.

The three-dimensional map maker 10 generates positional information of the stage part of the XYZ stage 2 and outputs it to the scan controller 3. Simultaneously, the three-dimensional map maker 10 converts the modulated signal voltage from the modulated low voltage signal processor 14 corresponding to the generated positional information into a digital value and takes it in, thereby creating a three-dimensional map. Further, it performs signal processing such as normalizing, which will be described later.

The function of a deconvolution processor 20 will be described.

As shown in FIG. 3, 45 three-dimensional voxels are set to the beam waist in the vicinity of the measurement point and upper and lower portions thereof, and each of the three-dimensional voxels is weighted in proportion to the light intensity in its position, thereby creating a convolution kernel. This convolution kernel is determined by the NA of the objective lens. The three-dimensional map is approximated as a convolution of a true image, which is a three-dimensional distribution of an absorbing substance, and a convolution kernel.

The deconvolution that is inverse operation of the convolution is calculated by a computer mounting the software "Huygens Essential" by Scientific Volume Imaging. It is not limited to this computer software. For processing the deconvolution, there exist various publicly known algorithms. It is possible to use any kind of deconvolution calculation method such as a method to calculate the convolution kernel from the NA of an objective lens or the refractive index of a medium, a method to actually measure the convolution kernel with a small bead being a specimen, or a blind deconvolution that does not need setting of the convolution kernel.

For three-dimensional deconvolution processing, a large number of MAC (multiply and accumulation) operations is needed. Other than the method by the computer mounting the computer software used in this embodiment, processing is also possible by an electronic circuit formed including a digital signal processor (DSP) device capable of performing the MAC operation at high speed, or similarly by an electronic circuit formed including a field programmable gate array (FPGA) device. It is also possible to accelerate the processing speed using a graphics processing unit (GPU).

In this embodiment, the convolution kernel constituted of 45 three-dimensional voxels is set, but it is needless to mention that the processing becomes more complete by setting a convolution kernel constituted of a large number of three-dimensional voxels including voxels of positions where the light intensity is lower. Further, setting of three-dimensional voxels more finely than a diffraction limit, a resolution beyond the diffraction limit can be obtained. However, this increases the processing time. It is desirable to set a convolution kernel that is commensurate with a demanded quality.

When the light source fluctuates, it affects a minute differential signal. A signal processing function set in the three-dimensional map maker 10 is used to divide the differential signal voltage by the reference signal voltage so as to cancel fluctuation of the light source. This is to normalize the differential signal voltage representing a light absorption amount by the reference signal voltage representing a light transmission amount of when there is no light absorption. By this normalization processing, a three-dimensional image that is not affected by fluctuation of the light source can be obtained.

In this embodiment the XYZ stage is employed as the scanning device to relatively move the specimen and the measurement point, but when the present invention is implemented it can be replaced with another scanning device having the same function as the XYZ stage. One of other scanning devices has a structure to scan the measurement point while fixing the biological specimen, that is, to scan while moving the optical flux using a galvano mirror or a polygon mirror. Another one of them has a structure to fix the measurement point and mount the specimen on an XYZ three-dimensional stage for scanning it. Moreover, it is also possible to combine the both methods. It is sufficient when the driving method is selected for each of scanning axes, and the specimen and the measurement point can be moved relatively while scanning the three axes.

The light source is not limited to LED lamps. Any lamp used as a light source in a microscope such as a halogen lamp, a mercury lamp, or the like can be used. A wavelength to be absorbed is selected with respect to a substance desired to be observed. For example, when it is desired to visualize a distribution of protein, a light source emitting a wavelength of 280 nm is selected, which absorbs amino acids tryptophan and tyrosine. In a certain light source, a light chopper that physically cuts a light intermittently is used as the light source modulating control device 5, instead of the electronic circuit.

Figure 5:
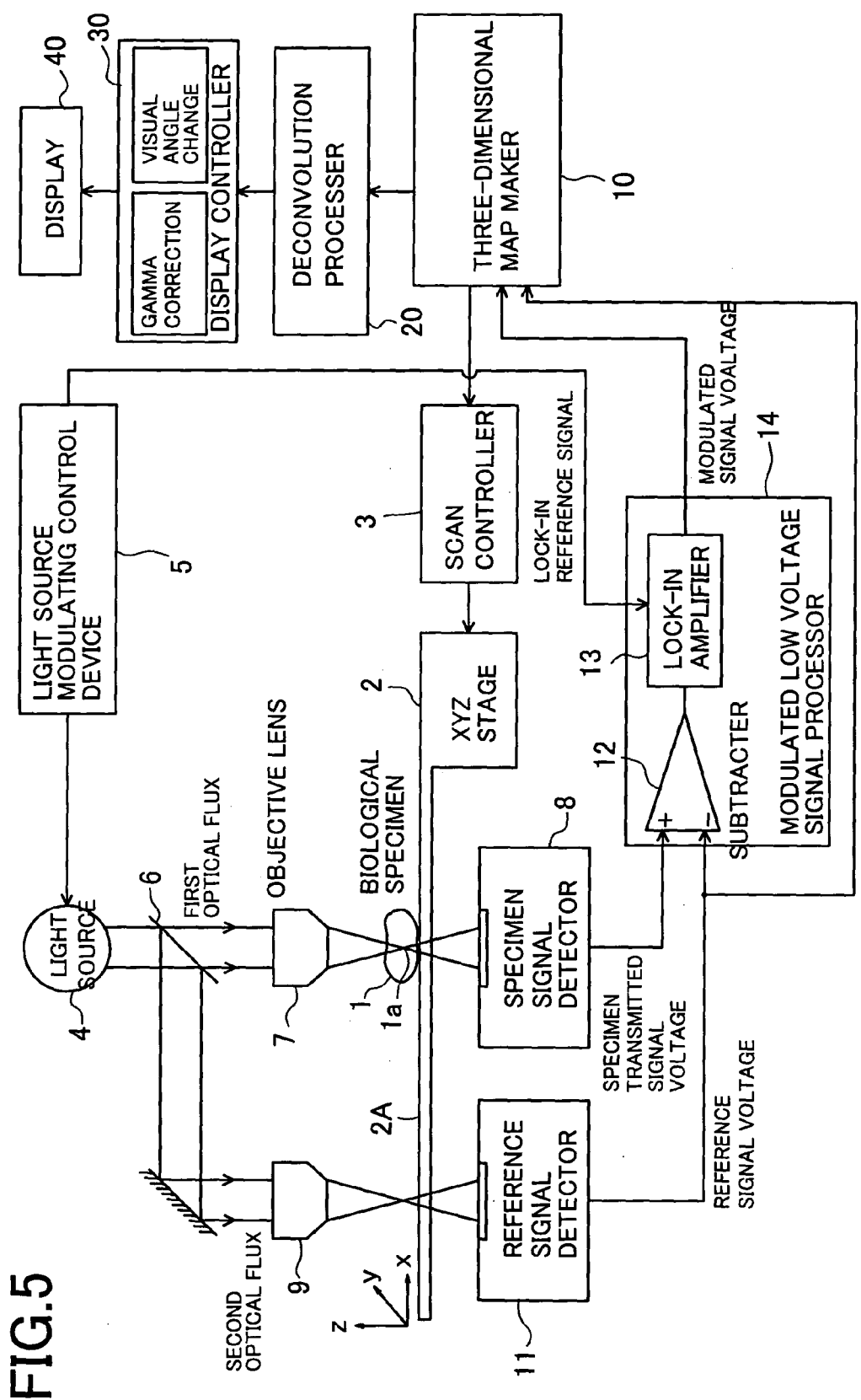
FIG. 5 is a block diagram showing a structure of a second embodiment of the present invention.

FIG. 5 shows a structure of a second embodiment and is a schematic diagram of a microscope and a processing apparatus. This embodiment only differs from the first embodiment in the structure to obtain the reference signal voltage and addition of a display part, and thus components having the same functions as those in the first embodiment are given the same reference numerals here, and their description is omitted appropriately. Although not shown in the diagram, a computer controlling a three-dimensional map maker 10 and a deconvolution processor 20, a pointing device, and so on are provided.

The biological specimen 1 is mounted on a stage part 2A of an XYZ stage 2 that is three-dimensionally drivable. The stage part 2A is made of a transparent material with high light transmittance. The XYZ stage 2 is controlled by a scan controller 3 which operates by instruction from the three-dimensional map maker 10.

An optical flux radiated from a light source is branched into an optical flux for specimen observation (hereinafter referred to as a first optical flux) and a reference optical flux (hereinafter referred to as a second optical flux) by a beam splitter 6. The first optical flux is focused at one point (measurement point) 1a in the specimen space of the specimen 1 by an objective lens 7. The optical flux passed through the specimen 1 is photoelectrically converted into a specimen transmitted signal voltage in a specimen transmitted signal detector 8. A reference signal detector 11 which detects the second optical flux is formed of an objective lens 9 disposed in parallel to the optical system of the first optical flux, the stage part 2A of the XYZ stage 2 extended for detection of reference signal, and the reference signal detector 11. The second optical flux passes through a place where no specimen exists and is photoelectrically converted into a reference signal voltage by the reference signal detector 11. The processing thereafter is similar to that in the first embodiment.

For displaying an obtained three-dimensional image, a display controller 30 and a display 40 are provided for achieving a function to correct gamma of an image and a function to change and display a visual angle.

The function to correct gamma of an image and display it and the function to change and display a visual angle will be described. An image is displayed on the display with enhanced contrast so that the observer can recognize a minute difference in absorption. A publicly known image processing technique is used for enhancing the contrast. For example, on the display, it is possible to perform display by assigning a black-and-white gradation or color. That is, a three-dimensional image of a biological specimen that is seen almost transparent when seen by the naked eye is displayed on the display while giving a large difference of contrast to a minute difference in absorption. Furthermore, when the observer observes while increasing contrast partially, it is structured to correct the gamma value indicating a relationship between data and displayed contrast, and performing display again. Further, using an affine conversion and rendering function, it is structured to rotate the three-dimensional image of the biological specimen and display again an image seen from a desired visual angle.

In this embodiment, after a three-dimensional image is obtained by the microscope, when one point in an image is specified, the scanner scans a narrow space region around the specified point as a center. Thus, the image of the specified point is measured over time. The narrow space region is a region that is minimally required for the deconvolution, and is set considering the size of the convolution kernel used. If necessary, a graph with a horizontal axis being time and a vertical axis being light absorption at the specified point is obtained. Further, it is also possible to circularly measure plural specified points regularly.

Figure 6:
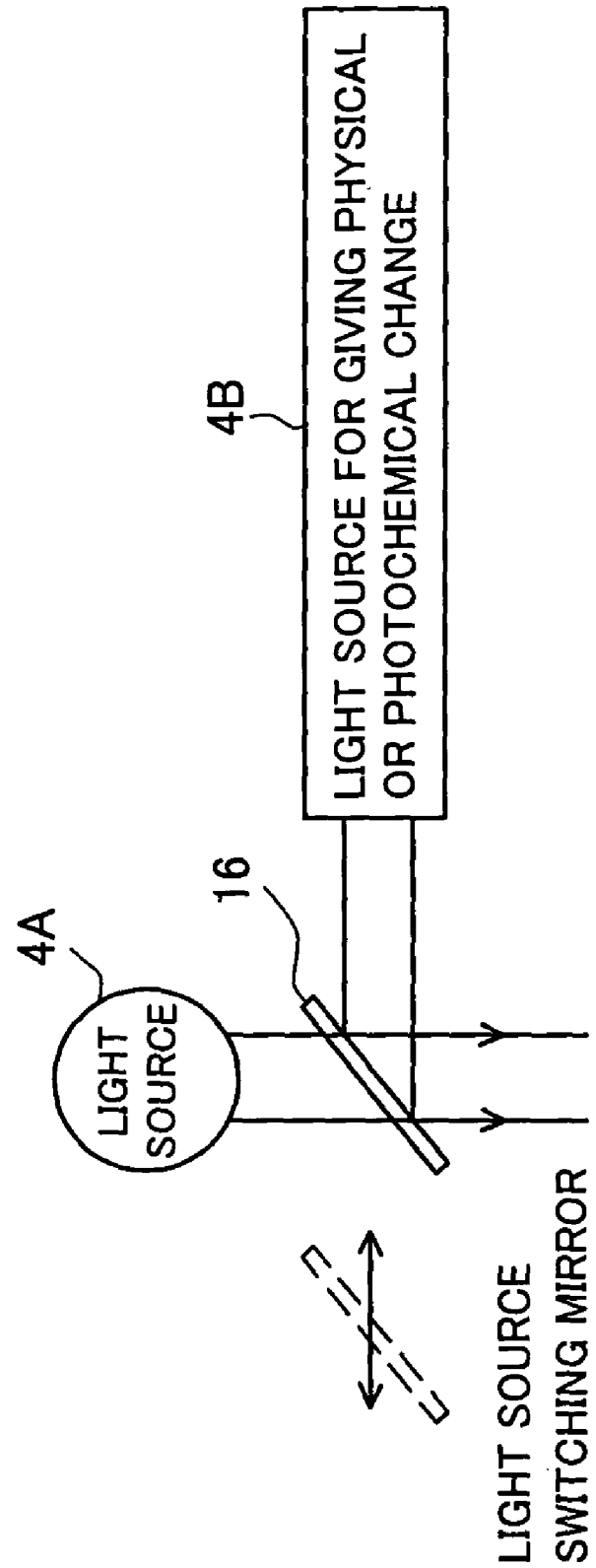
FIG. 6 is a diagram showing a light source unit in which a light source for giving a physical or photochemical change is provided aside.

As an application of this device, it is possible to achieve a device which forcibly gives a physical or photochemical change such as stimulation or processing. FIG. 6 shows a light source beside which a light source for giving a physical or photochemical change is disposed. The structure except the light source is the same as in FIG. 4. This device is structured such that a light source switching mirror 16 is inserted in the optical path between the beam splitter 6 and the objective lens 7 of FIG. 5, and a light source 4A for measurement and a light source 4B for forcibly giving physical or photochemical change are switched one to the other by the light source switching mirror 16 inserted in the optical path.

According to the application device, a positional resolution is lower than that when the image is obtained, but it is possible to make a physical change such as heating by a high-intensity light or a photochemical change by irradiation of a light having a different wavelength, for example an ultraviolet ray, in an arbitrary position of a biological specimen.

After a three-dimensional image is obtained with an observation light in advance, when an arbitrary point on this image is specified by the pointing device, three-dimensional coordinates thereof are sent to the scanning controller to move the stage part of the XYZ stage to the specified position, and thereby a focusing point (measurement point) of an optical flux can be matched with the specified position of the specimen. A specific organelle or the like which has been conventionally difficult to be discriminate due to a small difference in light absorption can be selectively stimulated and processed.

As an example of processing, a dye at a specific position in the specimen can be quenched. Further, regarding connection or splitting of nucleic acid that is necessary for genetic manipulation, this device can be used, instead of a conventionally used enzyme method (connection by ligase or splitting by restriction enzyme), to perform connection or splitting of nucleic acid at a certain position using a carboxyuracil molecule and a light with a wavelength of 366 nm and a light with a wavelength of 302 nm.

Figure 7:
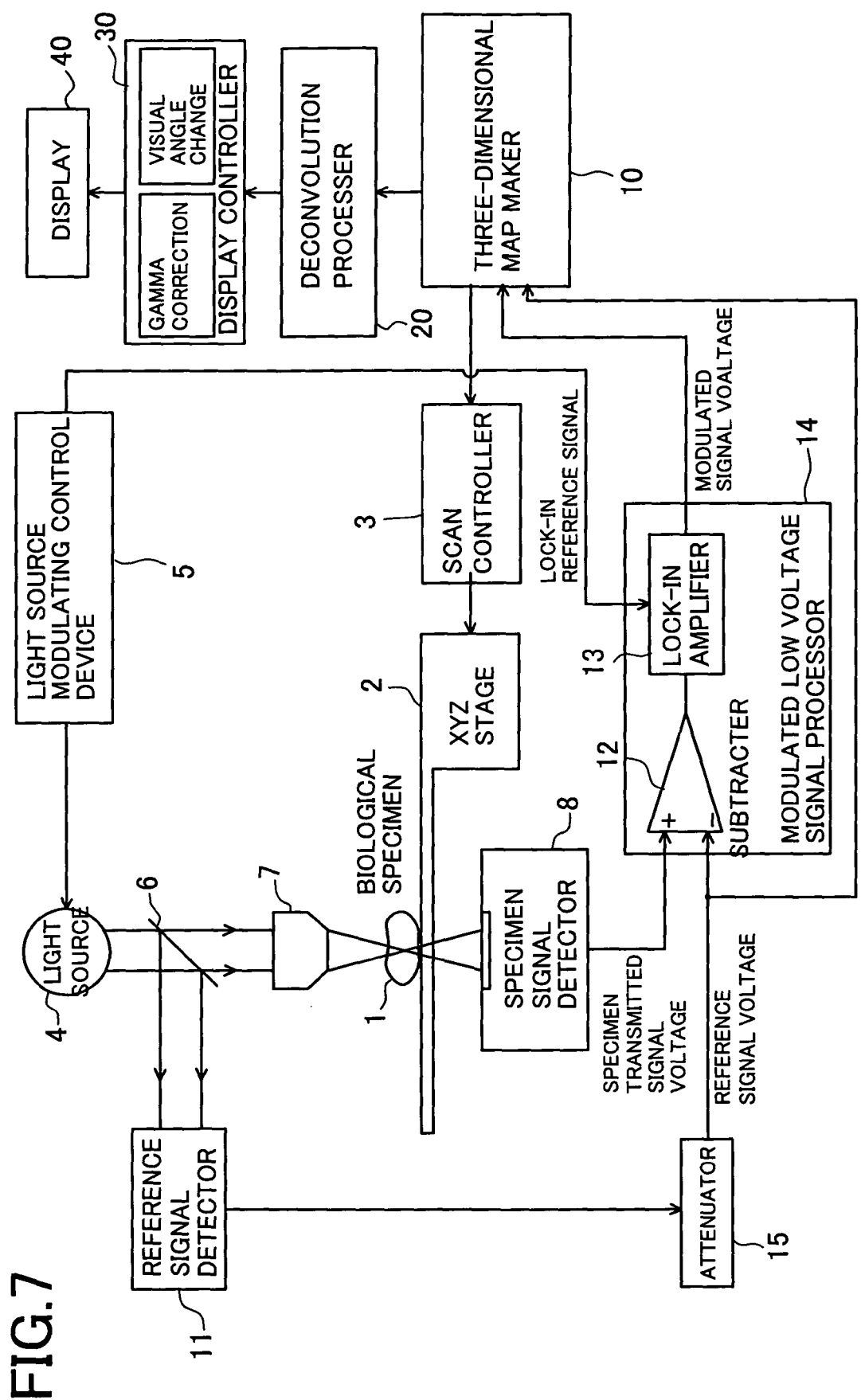
FIG. 7 is a block diagram showing a structure of a third embodiment of the present invention.

FIG. 7 shows a structure of a third embodiment and is a block diagram of a microscope and a processing apparatus. Here, for the processing apparatus, the light source switching means of FIG. 6 is applied. This embodiment is different in the means for obtaining a reference signal voltage, as compared to the above-described second embodiment. Only the means for obtaining a reference signal voltage will be described, and description of other parts are omitted.

An optical flux from a light source is branched into two optical fluxes for specimen measurement and reference by a beam splitter 6. The optical flux for reference is photoelectrically converted and amplified by the reference signal detector 11. An output of the reference signal detector 11 is inputted to a subtracter 12 via an attenuator (level adjustor) 15.

Prior to observation, the attenuation factor of the attenuator 15 is adjusted so that a positive input and a negative input of the subtracter 12 become equal in a state that a specimen 1 is not mounted in. In this operation a reference signal voltage used for observation is obtained.

An XYZ stage 2 is used in this embodiment. It is not limited to this method because it is sufficient as long as the specimen 1 and the measurement point where the optical flux is focused are moved relatively and scanned. It is possible to employ a method to fix the specimen 1 and scan while moving an optical flux using a galvano mirror or the like, a method performing YZ scanning using a movable objective lens like one employed as a pickup for CDs, or the like.

Figure 8:
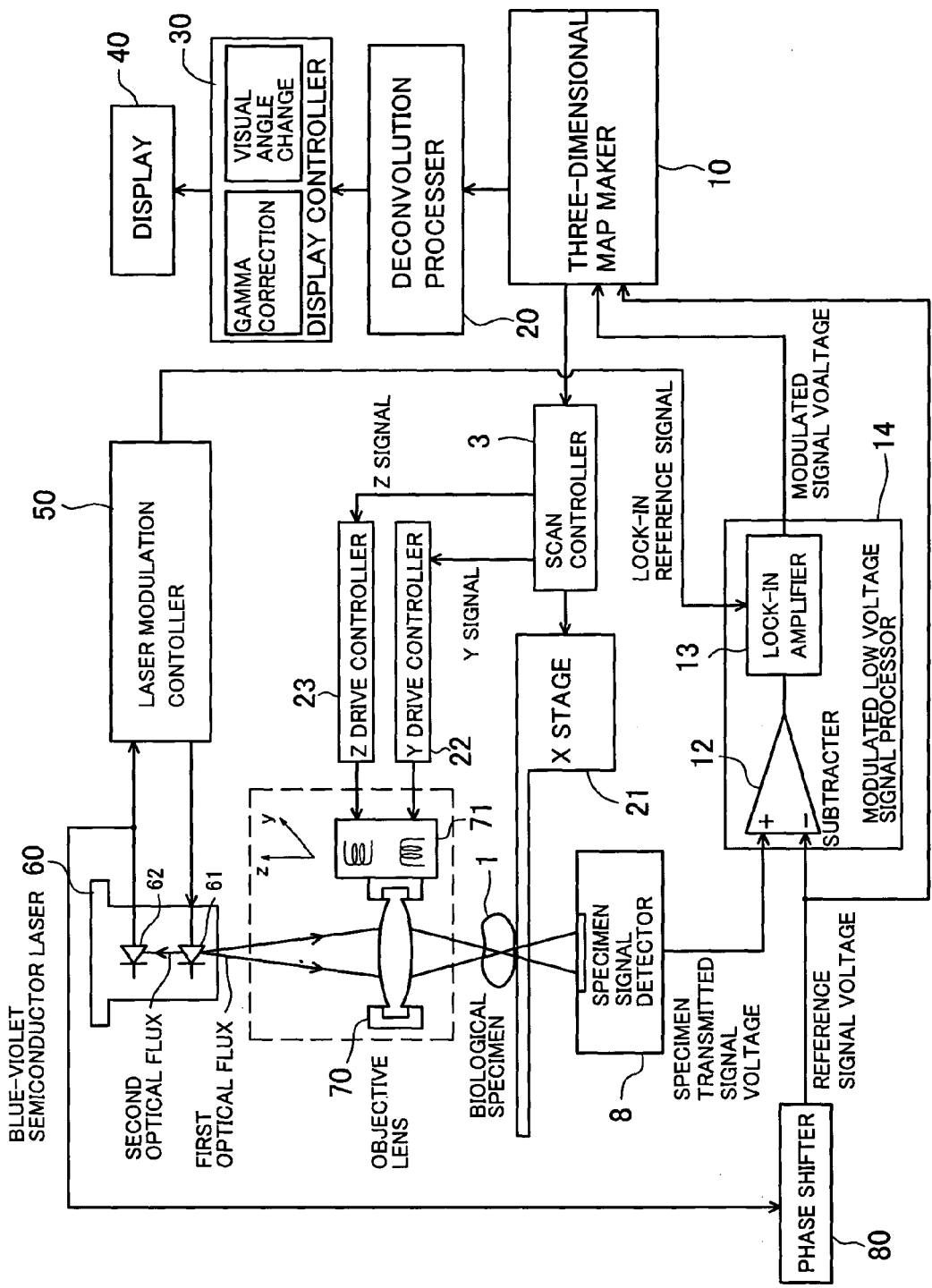
FIG. 8 is a block diagram showing a structure of a fourth embodiment of the present invention.

FIG. 8 shows a structure of a fourth embodiment and is a block diagram of a microscope and a processing apparatus. Here, for the processing apparatus, the light source switching means of FIG. 6 is applied.

Three-dimensional scanning is achieved by a movable objective lens moving in YZ directions and an X stage, and a reference signal voltage is generated from a monitor diode mounted in a blue-violet semiconductor laser.

They are a compact microscope and a compact processing apparatus applying the three-dimensional image obtaining device. As another application example, it can be used for an observation module forming an image obtaining part as one element of a biomedical related measurement apparatus, such as a device for tracking branching processes of a (ES or iPS) cell or a monitoring device of a cell culture apparatus.

The biological specimen 1 is mounted on an X stage 21 that is drivable in one dimension. As a semiconductor laser 60, a laser emitting diode 61 and a monitor diode 62 are mounted in a single element. A second optical flux emitted to the side beyond the laser emitting diode 61 is guided to the monitor diode 62 internally, and the light intensity of a first optical flux emitted on a front face is monitored.

The laser emitting diode 61 is controlled by a three-dimensional map maker 10 and a laser modulation controller 50, and radiates the first optical flux which is amplitude modulated with a predetermined frequency. The first optical flux is focused to a biological specimen 1 by a movable objective lens 70. The movable objective lens 70 is structured to be movable by a voice coil 71 to which an aspherical plastic lens 70 is assembled. The movable objective lens 70 is an objective lens capable of scanning two-dimensionally via a Y drive controller 22 and a Z drive controller 23 by instruction from the three-dimensional map maker 10.

In this embodiment, the movable objective lens 70 is used for two-dimensional scanning in Z axis and Y axis, and it has lower linearity since it is not controlled with negative feedback. A mechanism to correct the linearity of the Z drive controller 23 and the Y drive controller 22 is mounted.

An optical flux focused on the biological specimen 1 is photoelectrically converted and amplified by a specimen transmitted signal detector 8 as a main detector. The reference signal voltage is obtained from the monitor diode 62 incorporated in the semiconductor laser 60. The monitor diode 62 is originally provided for monitoring an emitted light from the laser emitting diode 61 and performs control with feedback so that the laser emitting diode 61 oscillates stably.

Also in this embodiment, the laser modulation controller 50 is connected and used for the purpose of suppressing fluctuation. Furthermore, in this embodiment, it is used for obtaining the reference signal voltage, and the monitor diode 62 is connected to the subtracter 12 via a phase shifter 80.

Prior to observation, in a state that the specimen 1 is not mounted on the stage, gain and a phase shift amount are adjusted so that the positive input and the negative input of the subtracter 12 have equal amplitudes and phases. In this embodiment, it is structured to adjust a phase difference generated by the difference in circuit structures of the specimen transmitted signal detector 8 and the monitor diode 62 by the phase shifter 80.

According to this embodiment, due to the lightweight and compact structures, the three-dimensional image obtaining device is applicable as an observation module that forms a part of a biomedical related measurement apparatus, besides stand alone microscope and processing apparatus.

The structures forming the present invention are not limited to the above-described embodiments. Replaceable means will be described below.

(1) As means for creating the local light intensity distribution in the vicinity of the measurement point, an optical flux may be focused at the measurement point by a concave mirror, besides focusing at the measurement point by the objective lens. Further, use of a phase shift mask technique, which is used for exposure of a semiconductor, allows to create the local light intensity three-dimensional distribution at the measurement point. A structure having a center part formed of a transparent material and a member that shifts a phase by a half wavelength surrounding the center part in a ring-belt shape is disposed on a mask, and when this mask is illuminated and reduced imaging is performed by an imaging lens at the measurement point, a minute local light intensity three-dimensional distribution is obtained at the measurement point. The light intensity distribution having a dual structure generated in the vicinity of the measurement point can be used as the convolution kernel.

(2) When a lens is disposed in front of the specimen transmitted signal detector and the reference signal detector, and the optical flux is narrowed, photoelectrical conversion can be performed by a small detector. Furthermore, a light scatterer may be disposed in front of the aforementioned detector so as to uniformize the optical flux for photoelectrical conversion.

When it is desired to selectively enhance and observe a specific structure, the present invention can be implemented using an antibody or nucleic acid, which is marked with a dye absorbing an observation light, or a dye for selectively staining a certain structure. Thus, such aspects are included in implementation of the present invention.

EXPLANATION OF THE LEGENDS 1 biological specimen
2 stage
3 scan controller
4 light source
5 light source modulating control device
6 half mirror
7, 9 objective lens
8 specimen transmitted signal detector
10 three-dimensional map maker
11 reference signal detector
12 subtracter
13 lock-in amplifier
14 modulated low voltage signal processor
15 reference signal generator
20 deconvolution processor

What is claimed is:

1. A three-dimensional image obtaining device, in which a biological material that is almost transparent is mounted as a specimen, for obtaining a three-dimensional image from an attenuation amount of a transmitted light through the specimen, the device comprising:
   a light source emitting an optical flux with light intensity being amplitude modulated by a predetermined frequency;
   an objective lens focusing the optical flux at a measurement point in the specimen to generate a local intensity distribution in the vicinity of the measurement point;
   a means for three-dimensionally scanning the specimen and the measurement point relatively;
   a modulated low voltage signal processor calculating a difference between a reference signal voltage equivalent to a transmitted light amount of the optical flux of when there is no specimen and a specimen transmitted signal voltage equivalent to a transmitted light amount of the optical flux of when there is a specimen, and outputting a modulated signal voltage equivalent to a minute light attenuation amount of the optical flux corresponding to position coordinates of the measurement point to be scanned;
   a means for making a three-dimensional map using the modulated signal voltage corresponding to the position coordinates of the measurement point; and
   a means for making a three-dimensional image of the specimen from the three-dimensional map by either a deconvolution using a convolution kernel obtained from a light intensity distribution image in the vicinity of the measurement point or a blind deconvolution which does not initially set a convolution kernel.

2. The three-dimensional image obtaining device according to claim 1, further comprising
   a display controller comprising a means for displaying the three-dimensional image of the specimen on a display, correcting gamma of the three-dimensional image, and displaying the three-dimensional image again, and a means for changing a visual angle of the three-dimensional image and displaying the three-dimensional image again.

3. The three-dimensional image obtaining device according to claim 1,
   wherein the deconvolution is performed by any one of a computer having three-dimensional deconvolution computer software, an electronic circuit structured including a digital signal processor (DSP), and an electronic circuit structured including a field programmable gate array (FPGA).

4. The three-dimensional image obtaining device according to claim 1,
   wherein the three-dimensional scanning means is formed of an XYZ three-dimensional stage mounting the specimen.

5. The three-dimensional image obtaining device according to claim 1,
   wherein the three-dimensional scanning means is formed of a one-dimensional stage of X axis mounting the specimen and a movable objective lens capable of scanning two-dimensionally in Y axis and Z axis.

6. The three-dimensional image obtaining device according to claim 1,
   wherein the three-dimensional scanning means is an optical flux three-dimensional scanning means for scanning an optical flux three-dimensionally in XYZ axis.

7. The three-dimensional image obtaining device according to claim 1,
   wherein the modulated low voltage signal processor divides a differential signal voltage between a specimen transmitted signal voltage and a reference signal voltage by the reference signal voltage to normalize the differential signal voltage.

8. The three-dimensional image obtaining device according to claim 1,
   wherein the modulated low voltage signal processor is structured including a lock-in amplifier.

9. The three-dimensional image obtaining device according to claim 1,
   wherein the reference signal voltage is a light detection output of an optical flux which is branched from the optical flux emitted from the light source and does not transmits through the specimen.

10. The three-dimensional image obtaining device according to claim 1,
wherein the light source is formed of a semiconductor laser, and the reference signal voltage is generated from a monitor diode mounted in the semiconductor laser.

11. A three-dimensional processing apparatus, comprising a three-dimensional image obtaining device, in which a biological material that is almost transparent is mounted as a specimen, for obtaining a three-dimensional image from an attenuation amount of a transmitted light through the specimen, specifying position coordinates of an arbitrary point in a specimen space of a biological specimen that is almost transparent, and optically stimulating and/or optically processing the arbitrary point,
wherein the three-dimensional image obtaining device comprises:
a light source emitting an optical flux with light intensity being amplitude modulated by a predetermined frequency;
an objective lens focusing the optical flux at a measurement point in the specimen to generate a local intensity distribution in the vicinity of the measurement point;
a means for three-dimensionally scanning the specimen and the measurement point relatively;
a modulated low voltage signal processor calculating a difference between a reference signal voltage equivalent to a transmitted light amount of the optical flux of when there is no specimen and a specimen transmitted signal voltage equivalent to a transmitted light amount of the optical flux of when there is a specimen, and outputting a modulated signal voltage equivalent to a minute light attenuation amount of the optical flux corresponding to position coordinates of the measurement point to be scanned;
a means for making a three-dimensional map using the modulated signal voltage corresponding to the position coordinates of the measurement point; and
a means for making a three-dimensional image of the specimen from the three-dimensional map by either a deconvolution using a convolution kernel obtained from a light intensity distribution image in the vicinity of the measurement point or a blind deconvolution which does not initially set a convolution kernel.

* * * * *